United States Patent
Gallagher et al.

[11] Patent Number: 6,140,518
[45] Date of Patent: Oct. 31, 2000

[54] STEROID BISPHOSPHONATES

[75] Inventors: James Anthony Gallagher, Crosby; Jonathan Paul Granville Moore, Brixham; Wayne Barry Bowler, Liverpool; Philip Charles Bulman Page, Loughborough, all of United Kingdom

[73] Assignee: The University of Liverpool, Liverpool, United Kingdom

[21] Appl. No.: 09/147,430

[22] PCT Filed: Jun. 26, 1997

[86] PCT No.: PCT/GB97/01748

§ 371 Date: Apr. 8, 1999

§ 102(e) Date: Apr. 8, 1999

[87] PCT Pub. No.: WO98/00438

PCT Pub. Date: Jan. 8, 1998

[30] Foreign Application Priority Data

Jun. 28, 1996 [GB] United Kingdom .................. 9613722

[51] Int. Cl.[7] .............................. A61K 31/56; C07J 51/00
[52] U.S. Cl. ......................... 552/506; 514/169; 514/178; 514/182
[58] Field of Search ............................ 552/506; 514/169, 514/178, 182

[56] References Cited

U.S. PATENT DOCUMENTS 5,391,776  2/1995  Ueno et al. .............................. 552/507

FOREIGN PATENT DOCUMENTS

| 0 496 520 | 7/1992 | European Pat. Off. . |
| 0 548 884 | 6/1993 | European Pat. Off. . |
| 0 555 845 | 8/1993 | European Pat. Off. . |
| 0555845 | 8/1993 | European Pat. Off. . |
| 2 683 527 | 5/1993 | France . |
| 92 05187 | 4/1992 | WIPO . |

OTHER PUBLICATIONS

Guervenou et al., Phosphorus, Sulfur and Silicon and the Related Elements, 88(1–4):1–13 (1995).

*Primary Examiner*—Barbara Badio
*Attorney, Agent, or Firm*—Bacon & Thomas

[57] ABSTRACT

Bisphosphonate derivatives of hydroxy steroids which are bone resorption inhibitors or bone formation stimulators, the derivatives having at least one group A in place of a hydroxy group on the steroid molelcule, where A is a group of forumla (A) where X is: (i) St—O—CO— where St is the residue of the hydroxy steroid given by removal of an OH group; or (ii) $R^1$—O—CO— where $R^1$ is an alkyl, alkenyl, cycloalkyl, aralkyl or aryl group, any of which may optionally be substituted, and the salts and solvates of these compounds. The steroid is typically 17β-oestradiol, oestrone, testosterone, norethindrone, androsterone, norethandrolone or nandrolone. The derivatives can be used in the treatment of bone disorders such as osteoporosis.

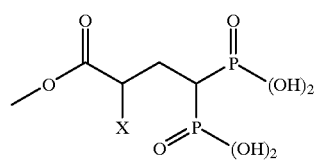

(A)

8 Claims, No Drawings

STEROID BISPHOSPHONATES

This application is a 371 of PCT/GB97/01748 filed Jun. 26, 1997.

This invention concerns steroid derivatives and in particular bisphosphonate derivatives of hydroxy steroids for use in the prevention or treatment of osteoporosis and related bone disorders.

Hydroxy steroids such as oestradiol and testosterone have been proposed for use in the treatment of osteoporosis, either by inhibition of bone resorption or stimulation of bone formation, and bisphosphonates such as disodium etidronate and clodronate are also known as bone resorption inhibitors. Certain bisphosphonate derivatives of steroids have also recently been proposed for these purposes in EP-A-0496520 and EP-A-0548884. In the compounds of EP-A-0496520 the steroidal group is linked to the bisphosphonate group by a carbamate or carbonate group, and EP-A-0548884 describes steroid bisphosphate ethers.

We have now found a new group of bisphosphonate derivatives of such steroids which are linked by a carboxyl group and, by virtue of the affinity of the bisphosphonate groups for bone, have the potential to target the active steroid selectively on bone and then release the active material in situ by hydrolysis. The compounds of the invention are thus of interest in the prevention or treatment of osteoporosis and other bone disorders such as Paget's disease, bone metastases and malignant hypercalcaemia.

The compounds of the invention are derivatives of hydroxy steroids which are themselves bone resorption inhibitors or bone formation stimulators and thus useful in the prevention or treatment of osteoporosis, the derivatives having at least one group A in place of a hydroxy group on the steroid molecule, where A is a group of the formula

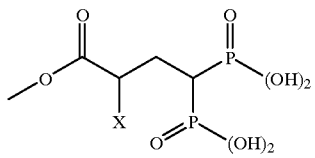

(A)

where X is:

(i) St—O—CO— where St is the residue of the hydroxy steroid given by removal of an OH group, (ii) $R^1$—O—CO— where $R^1$ is an alkyl, alkenyl, cycloalkyl, aralkyl or aryl group, any of which may optionally be substituted, or (iii) a hydrogen atom. The invention also includes salts and solvates of these compounds.

The compounds of the invention may thus have the formula St-A where St and A are as defined above. Particular groups of compounds of interest are those of the formulae:

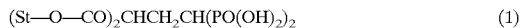
(1)

(2)

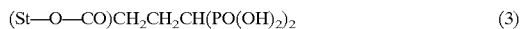
(3)

Where the steroid contains more than one hydroxy group, only one is usually replaced by a group A, but the invention includes derivatives of such compounds in which two or more hydroxy groups are replaced by A groups.

The structural variety of the compounds of the invention allows their hydrolysis properties to be modulated as required. For example, most known steroid-bisphosphonate conjugates, particularly oestradiol-biphosphonates, hydrolyse very rapidly whereas slower hydrolysis and hence slower release of the steroid is often desirable. Compounds of formula (1) above such as the compound (4) below which contains two steroid units are resistant to hydrolysis and thus advantageous when a slower rate of steroid release is required. On the other hand, compounds containing only one steroid unit are less resistant to hydrolysis and thus more suitable when rapid steroid release is required. The compounds of formula (1) also enable two different steroid units to be included in the same molecule, and this allows steroids of different activities to be delivered at the same time.

The parent hydroxy steroid may be an oestrogen, androgen, anabolic steroid, glucocorticoid or progestagen which inhibits bone resorption or stimulates bone formation, such as for example 17β-oestradiol, oestrone, testosterone, norethindrone, androsterone, norethandrolone and nandrolone. These compounds generally have a hydroxy group at the 3- or 17- position or both, and further examples of hydroxy steroids which may be used are listed in EP-A 0496520.

In the group X, $R^1$ may be a $C_{1-6}$ alkyl (e.g. methyl, ethyl, isopropyl or t-butyl), $C_{2-6}$ alkenyl (e.g. allyl), $C_{3-8}$ cycloalkyl (e.g. cyclopentyl or cyclohexyl), phenyl ($C_{1-6}$) alkyl or a mono- or bicyclic aryl group (e.g. phenyl or naphthyl). The alkyl and alkenyl groups may for example be substituted by one or more halogen atoms (e.g. chlorine) and the cycloalkyl groups by one or more $C_{1-4}$ alkyl groups or halogen atoms (e.g. chlorine). The aryl groups may be substituted by one or more hydroxy groups, as in naphthol.

The compounds of the invention are capable of forming salts with bases and examples of such salts are alkali metal (e.g. sodium) and alkaline earth metal (e.g. calcium) salts. Some compounds of the invention exist in enantiomeric forms and all such forms are included.

Particular compounds of importance have the following formulae:

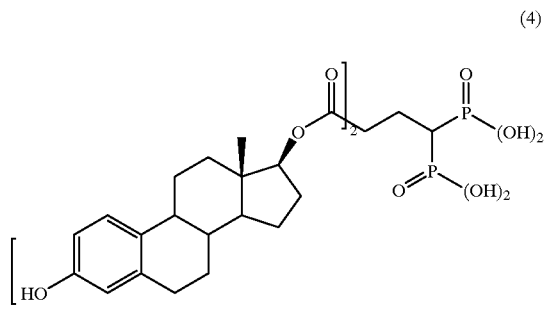
(4)

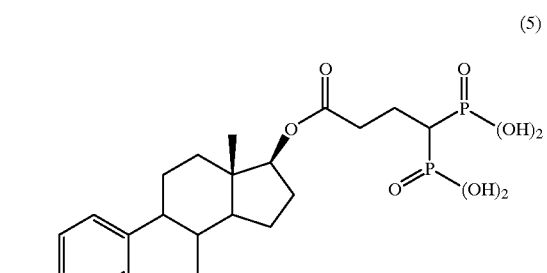
(5)

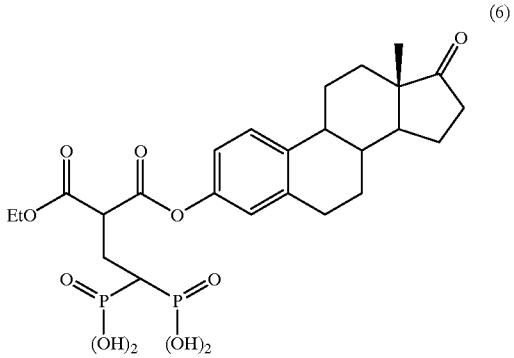
(6)

The compounds of the invention are useful in the prevention or treatment of osteoporosis and the other bone disorders referred to above in man and animals and they may be formulated for these purposes as pharmaceutical compositions together with one or more pharmaceutically acceptable carriers, excipients or diluents. The active ingredient in these compositions may for example be a compound (4), (5) or (6) shown above.

The pharmaceutical compositions of the invention may be in a form suitable for oral, buccal, parenteral or topical administration.

For oral administration, compositions may be in the form of, for example, tablets, lozenges or capsules containing pharmaceutically acceptable excipients such as binding agents, fillers, lubricants, disintegrants or wetting agents. The tablets may also be coated by known methods. Liquid preparations for oral administration may be in the form of solutions, syrups or suspensions and may contain pharmaceutically acceptable additives such as suspending agents, emulsifying agents, non-aqueous vehicles and preservatives.

The compositions may also be formulated for use by injection and may be presented in unit dose form, e.g. in ampoules. The compositions for injection may be in the form of suspensions, solutions or emulsions, in oily or aqueous vehicles, and may contain formulatory agents such as suspending, stabilising, solubilising and/or dispersing agents.

The compositions may also be in a form suitable for topical administration, e.g. transdermal patches, ointments, creams and lotions.

The compounds of the invention may be administered in combination with other pharmaceutically active ingredients.

The total daily dosages of compounds of the invention employed in medicine will suitably be in the range 0.001–10.0 mg/kg bodyweight and these may be given in divided doses, i.e. 1–4 times per day.

Compounds of the invention in which X is a group (i), for example compounds of formula (1) above, may be prepared by transesterification of the carboxylic ester group of a compound of formula (7)

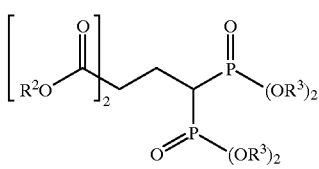
(7)

(where $R^2$ and $R^3$ are $C_{1-6}$ alkyl groups, e.g. ethyl, and may be the same or different) with the hydroxy steroid (StOH), to give a phosphonate ester (8) of the formula (St—O—CO)$_2$CHCH$_2$CH(PO(OR$_3$)$_2$)$_2$, followed by hydrolysis of the phosphonate ester group to give the desired bisphosphonic acid.

The transesterification of (7) may be effected in the presence of a base catalyst such as DMAP (dimethylaminopyridine), for example in a hydrocarbon solvent at any suitable temperature up to reflux.

When the parent hydroxy steroid contains a further hydroxy group which is to remain in the final product, this should be protested during the transesterification reaction (for example as a benzyl ether) and the protecting group subsequently removed.

The hydrolysis of the ester (8) may be carried out with a tri ($C_{1-6}$ alkyl) silyl halide such as trimethylsilyl bromide, for example in a halogenated hydrocarbon solvent.

The bisphosphonates (7) may be prepared by first reacting a methylene bisphosphonate (9)

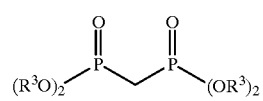
(9)

with paraformaldehyde (e.g. in the presence of a base catalyst such as diethylamine) followed by elimination of methanol to give a methylidene compound (10)

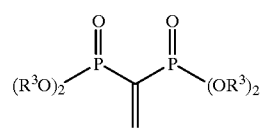
(10)

which is then reacted with a dialkylmalonate (in which the alkyl group is $R^2$ as defined above) in the presence of a base catalyst (e.g. sodium ethoxide).

Compounds in which X is a group (iii), for example compounds of formula (3) above may be prepared by esterification of the hydroxy steroid (StOH) with the acid (11)

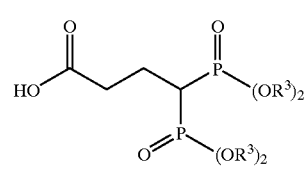
(11)

The reaction may be carried out in the presence of a base and an activating agent such as EDCI (N-(3-ethyldimethylaminopropyl)-N'-ethylcarbodiimide hydrochloride). The phosphonate ester groups may then be removed by hydrolysis as described above to give the required bisphosphonic acid.

Again, when the hydroxy steroid contains a further hydroxy group which is to be retained, it should be protected during the reaction and subsequently removed.

The acids (11) can be prepared from a methylidene compound (10) above by addition of a dibenzyl malonate, in the presence of a non-nucleophilic base catalyst, to give the ester (12)

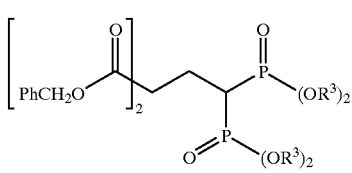

followed by hydrogenolysis (e.g. over palladium on carbon) and subsequent decarboxylation (e.g. by heating).

Compounds in which X is a group (ii), for example compounds of formula (2) above may be prepared from a malonate (13) of the hydroxy steroid $$R^1OCO.CH_2.CO.OSt \qquad (13)$$

by reaction with a methylidene compound (10) in the presence of a non-nucleophilic base to give the addition product (14)

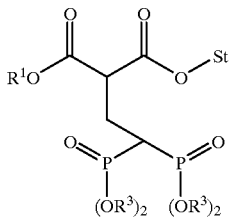

followed by removal of the phosphonate ester group by hydrolysis as described above to give the desired bisphosphonic acid.

The following examples illustrate the invention.

EXAMPLE 1

Synthesis of Tetraethyl ethylidene bisphosphonate (16)

(i)

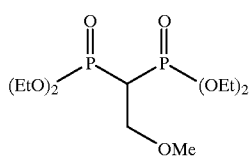

Tetraethyl methylene bisphosphonate (47.4 g, 0.165 mol, 1.0 equiv.), paraformaldehyde (24.75 g, 0.825 mol, 5.0 equiv.), diethylamine (17.1 ml, 12.1 g, 0.165 mol, 1.0 equiv.) were added to methanol (470 ml). The reaction mixture was heated at 60 °C. until the mixture became a colourless solution (30 minutes), and stirred for a further 15 hours at room temperature. The mixture was concentrated under reduced pressure, and toluene (150 ml) added. The solvent was removed under reduced pressure. The addition of toluene followed by a second concentrating process aided the removal of methanol from the crude viscous intermediate product 15. $\delta_H$(CDCl$_3$) 1.29 (12H, t, J=8, P—OCH$_2$C$\underline{H}_3$), 2.67 (1H, tt, $J_{H-P}$=24, $J_{H-H}$=5, P$_2$C$\underline{H}$CH$_2$OCH$_3$), 3.32 (3H, s, —OCH$_3$), 3.86 (2H, td, $J_{H-P}$=17, $J_{H-H}$=5, P$_2$CHC$\underline{H}_2$OCH$_3$), and 4.15 (8H, m, P—OC$\underline{H}_2$CH$_3$).

(ii)

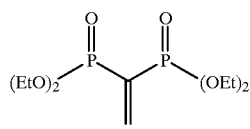

Toluene-p-sulfonic acid (0.15 g, catalytic) was added to a solution of crude tetraethyl (2-methoxy) ethylidene bisphosphonate 15 in toluene (250 ml). The reaction mixture was heated overnight, under reflux conditions, after this period of time elimination had gone to completion. The reaction mixture was washed with water (3×100 ml), and the solvent removed under reduced pressure to yield 16 as an oil (43.16 g, 88% for 2 steps); $v_{max}$ 3020, 2960, 1485, 1452, 1402, 1270 (b), and 1050 (b); $\delta_H$(CDCl$_3$) 1.30 (12H, t, J=8.0, P—OCH$_2$C$\underline{H}_3$), 4.0–4.2 (8H, m, P—OC$\underline{H}_2$CH$_3$), and 6.94 (2H, dd, trans $J_{P-H}$=40.0, cis $J_{P-H}$=36.4, P$_2$C=C$\underline{H}_2$); $\delta_C$(CDCl$_3$) 16.15 (4C, t, J=3.4, P—OCH$_2$$\underline{C}$H$_3$), 63.08 (4C, d, J=3.4, P—O$\underline{C}$H$_2$CH$_3$), 132.58 (1C, t, J=127, P—$\underline{C}$—P) and 149.11(1C, s, —P$_2$C=$\underline{C}$H$_2$); m.s. (CI) m/z 301 (M$^+$+H).

EXAMPLE 2

Synthesis of Hexa ethyl-[3,3-bis(oxycarbonyl)] propylidene bis[phosphonate] (17)

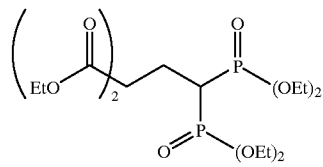

Sodium (0.23 g, 10 mmol, 0.1 equiv.) was dissolved in ethanol (100 ml) and stirred at 0° C. under a nitrogen atmosphere. The mixture was allowed to warm to ambient temperature until all the sodium had dissolved. The sodium ethoxide solution prepared in situ was transfered via a cannula to a solution of 16 (30.0 g, 100 mmol, 1.0 equiv.) and diethyl malonate (15.20 ml, 16.02 g, 100 mmol, 1.0 equiv.) in ethanol (50 ml). The reaction mixture was stirred under an atmosphere of nitrogen at ambient temperature for 30 minutes. The reaction mixture was washed with aqueous HCl 1M (3×100 ml) and extracted into CH$_2$Cl$_2$ (200 ml). The organic fraction was collected and dried with anh. MgSO$_4$, the solvent was removed under reduced pressure final traces of solvent were removed under high vacuum. The desired product 17 was isolated as an oil in excellent yield (43.8 g/95.1%). (Found: C 43.97 H 7.55, C$_{17}$H$_{34}$O$_{10}$P$_2$ requires: C 44.35 H 7.44); $v_{max}$ 3010, 1749, 1732, 1270 (b), and 1045 (b) cm$^{-1}$; $\delta_H$ (CDCl$_3$) 1.28 (6H, t, J=7.16, CO$_2$CH$_2$C$\underline{H}_3$), 1.35 (12H, t, J=7.12, PO$_2$CH$_2$C$\underline{H}_3$), 2.33–2.75 (3H, m), 3.97 (1H, t, J=7.68, —C$\underline{H}$(CO$_2$Et)$_2$), and 4.12–4.27 (12H, m); $\delta_C$(CDCl$_3$) 14.48 (2C, s, —CO$_2$CH$_2$$\underline{C}$H$_3$), 16.71 (4C, d, $J_{CP}$=PO$_2$CH$_2$$\underline{C}$H$_3$), 25.29 (1C, t, $J_{CP}$=5, —C$\underline{H}$CH$_2$CH—), 34.71 (1C, t, JCP=132, P—$\underline{C}$—P), 50.51 (1C, t, $J_{CP}$=8, —CH$_2$$\underline{C}$H(CO$_2$Et)$_2$, 61.97 (2C, s, —CO$_2$$\underline{C}$H$_2$CH$_3$), 63.22 (4C, t, $J_{CP}$=, PO$_2$$\underline{C}$H$_2$CH$_3$), and 169.31 (2C, s, —$\underline{C}$O$_2$Et); $\delta_P$CDCl$_3$)22.33; m/z (CI) 461 (M$^+$+H).

EXAMPLE 3

Synthesis of Tetraethyl {3,3-bis-[3-benzyloxy-estra-1,3,5-triene-17β-yloxycarbonyl]propylidene}bis[phosphonate] (18)

(18)

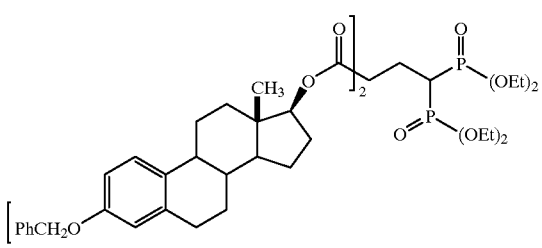

4-(N,N-dimethylamino)pyridine (0.013 g, 0.11 mmol, 0.1 equiv.) and 3-benzyl-17β-oestradiol (0.861 9, 2.39 mmol, 2.2 equiv.) were added to a solution of 17 (0.50 g, 1.09 mmol, 1.0 equiv.) in toluene (10 ml). The reaction mixture was heated under reflux for 11 days under an atmosphere of nitrogen. The solvent was removed under reduced pressure and the crude product absorbed onto silica gel. The product was purified by silica gel flash column chromatography, the eluent used was 1–3% methanol in $CH_2Cl_1$ the desired product was obtained as a viscous oil (0.80 g, 67%); $v_{max}$ 3017, 2936, 1724, 1605, 1498, 1203 (b), and 929; $δ_H(CDCl_3)$ 0.84 (3H, s, 18'—$CH_3$), 0.88 (3H, s, 18'—$CH_3$), 1.23–1.97 (21H, m), 1.35 (12H, t, J=7), 2.15–2.36 (13H, m), 4.72–4.81 (2H, m, 17'H), 5.05 (4H, s, —O$CH_2$Ph), 6.74 (2H, s, 4'H), 6.80 (d, 2H, J=9, 2'H), 7.23 (d, 2H, J=9, 1'H), and 7.30–7.47 (m, 10H); $δ_C(CDCl_3)$ 13.09, 13.20, 17.43, 17.51, 24.35, 26.19, 27.24, 28.29, 28.53, 30.82, 35.51 (t, $J_{CP}$=132, P$C$P), 37.95, 44.15, 44.31, 44.84, 50.80, 51.38 (t, $J_{CP}$=7.3, —CH$CH_2$CH(CO$_2$R)$_2$), 63.83 (t, $J_{CP}$=6.9, —CH$_2$$CH$(CO$_2$R)$_2$), 71.00, 85.02 (d, $J_{CP}$=10.4, PO$_2$$CH_2$CH$_3$), 113.39, 115.92, 127.42, 128.49, 128.89, 129.59, 133.73, 138.39, 138.95, 157.84, and 169.96 (d, $J_{CP}$=3.5, —CH($CO_2$R)$_2$); $δ_P(CDCl_3)$ 20.4; m/z (+ve ion FAB) 1094 (M$^+$+H, 100).

EXAMPLE 4

Synthesis of Tetraethyl {3,3-bis[estra-1,3,5-triene-3-hydroxy-17β-yloxycarbonyl]propylidene} bis[phosphonate]

(19)

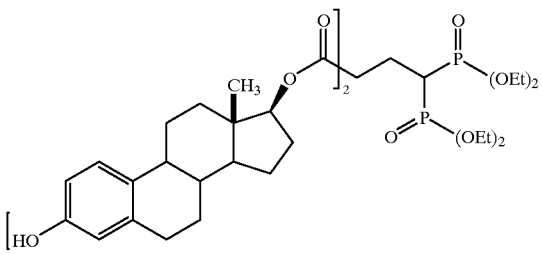

To a solution containing 18 (692 mg, 0.633 mmol, 1.0 equiv.) in teahydrofuran/methanol 1:1 (10 ml) was added 10% Pd/C (140 mg). The reaction mixture was shaken under an atmosphere of hydrogen (1 bar) for 6 hours. The reaction mixture was filtered, taken up into $CH_2Cl_2$ and washed with brine. The organic layer was collected and dried with anh. MgSO$_4$ and the solvent removed under reduced pressure. The product was purified further by silica gel flash column chromatography, eluted with 3–5% methanol in $CH_2Cl_2$. The solvent was once again removed and the product was produced as a foam under high vacuum (557 mg, 96.4%); (Found: C, 64.68; H, 7.76. $C_{49}H_{70}O_{12}P_2$ requires: C, 64.46; H, 7.73); $δ_H(CDCl_3)$ 0.775 (3H, s, 18'—$CH_3$), 0.781 (3H, s, 18'—$CH_3$), 1.15–1.87 (21H, m), 1.34 (12H, t, J=6.8, P—O$CH_2$$CH_3$), 2.09–2.33 (6H, m), 2.49 (2H,heptet, J=7.6, P$_2$CH$CH_2$CH(CO$_2$R)$_2$), 2.66 (1H, tt, $J_{P-H}$=24, $J_{H-H}$=7.2 P$_2$CH$CH_2$CH(CO$_2$R)$_2$), 2.81 (4H, m), 4.05 (1H, t, J=7.6, P$_2$CHCH$_2$C$H$(CO$_2$R)$_2$), 4.16–4.24 (8H, m, P—O$CH_2$CH$_3$) 4.71 (2H, q, 9.2, 17'H), 6.58 (2H, s, 4'H), 6.66 (2H, d, J=8, 2'H), and 7.08 (2H, d, J=8.8, 1'H); $δ_C(CDCl_3)$ 11.93 (1C, 18'C), 12.03 (1C, 18'C), 16.29 (4C, d, J=5, P—OCH$_2$$C$H$_3$), 23.22 (2C), 24.95 (1C, b—P$_2$CH$CH_2$CH—), 26.16 (2C), 27.18 (1C), 27.37 (1C), 29.53 (2C), 34.17 (1C, t, J=134, P—$C$—P), 36.81 (2C), 38.56 (2C), 42.98 (2C), 43.17 (1C), 43.68 (1C), 49.64 (2C) 50.23 (1C, t, J=9, P$_2$CHCH$_2$ $C$H(CO$_2$R)$_2$) 63.06 (4C, t, J=7, P—O$C$H$_2$CH$_3$), 83.95 (1C, 17'C), 84.09 (1C, 17'C), 112.77 (2C), 115.31 (2C), 126.22 (2C), 131.48 (2C), 131.53 (2C), 137.79 (2C), 154.23 (2C), and 168.84 (2C, —CO$_2$R); $δ_P(CDCl_3)$ 20.7(s); m/z (+ve ion FAB) 913 (M$^+$+H, 76), 159 (100) .

EXAMPLE 5

Synthesis of 3,3-Bis-(estra-1,3,5-trien-3-hydroxy-17β-yloxycarbonyl) propylidene bis(phosphonic acid) (20)

(20)

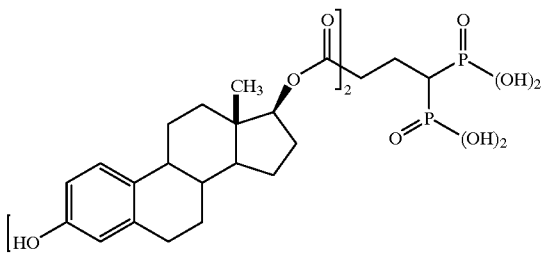

To a solution of 19 (250 mg, 0.275 mmol, 1.0 equiv. ) in CCl$_4$/CHCl$_3$ 1:1 (3 ml) was added trimethylsilyl bromide (1.24 ml, 1.47 g, 9.62 mmol, 35 equiv.) and the mixture stirred for 24 hours under a nitrogen atmosphere. Water (5 ml) was added and an off white solid formed. The precipitate was filtered and washed with cold water and $CH_2Cl_2$. The product was dried under high vacuum and obtained as an off white powder (206 mg, 94%) which decomposes at 180° C.; $δ_H(CD_3OD)$ 0.85 (3H, S, 181'—$CH_3$), 0.86 (3H, S, 18'—$CH_3$), 1.20 2.05 (21H, m), 2.10–2.30 (5H, m), 2.38–2.50 (3H, m), 2.70 2.81 (4H, m), 4.08 (1H, t, J=7, —CH$_2$C$H$(CO$_2$H)$_2$), 4.72 (2H, t, J=8, 17'H), 6.47 (2H, d, J=2, 4'H), 6.53 (2H, dd, J=9, J=2, 2'H), and 7.05 (2H, d, J=9, 1 'H); δC (CD$_3$OD) 12.64 (1C, 18'C), 12.71 (1C, 18'C), 24.22 (2C), 26.37 (1C, b, —P$_2$CH$CH_2$CH—), 27.44 (2C), 28.45 (2C) 28.52 (2C), 30.63 (2C), 36.79 (1C, t, J=127, P—$C$—P), 38.16 (2C,b), 40.18 (2C), 44.28 (1C, 13'C), 44.40 (1C, 13'C), 45.10 (2C), 50.94 (2C), 52.04 (1C, b, —$C$H(CO$_2$R)$_2$), 85.26 (1C, 17'C) 85.34 (1C, 17'C), 113.79 (2C), 116.08 (2C), 127.21 (2C) 132.36 (2C), 138.73 (2C), 155.94 (2C, 3'C), and 170.49 (2C, —CO$_2$R); $δ_P(CD_3OD)$ 22.6; m/z (—ve ion FAB) 799 (M$^-$—H, 100).

EXAMPLE 6

Synthesis of Tetraethyl [3,3 bis(benzyloxycarbonyl)]propylidene bis [phosphonate] (21)

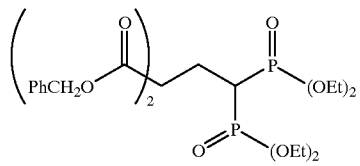

(21)

Tetraethyl ethylidene bisphosphonate 16 (1.00 g, 3.33 mmol, 1.0 equiv.), and dibenzyl malonate (0.83 ml, 0.946 g, 3.33 mmol, 1.0 equiv.) were dissolved in tetrahydrofuran (15 ml). Lithium bis(trimethylsilyl) amide solution in tetrahydrofuran (1M), (0.33 ml, 0.33 mmol, 0.1 equiv.), was added to the reaction mixture and stirred for one hour at room temperature. Saturated aqueous ammonium chloride (50 ml) was added to the reaction mixture and the product extracted into $CH_2Cl_2$ (100 ml). The organic layer was collected and dried with anh. $MgSO_4$, the solvent was removed under reduced pressure. The crude product was absorbed onto silica gel and purified by silica gel flash column chromatography, eluted with 2–3% methanol/$CH_2Cl_2$. The product was isolated as a colourless oil (1.12 g, 58% yield); $\delta_H$(CDCl$_3$) 1.30 (6H, t, J=7.1, —OCH$_2$CH$_3$), 1.31 (6H, t, J=7.1, —OCH$_2$CH$_3$), 2.37–2.74 (3H, m), 4.07–4.24 (9H, m), 5.14 (4H, s, —OCH$_2$Ph), and 7.24–7.35 (10H, m); $\delta_C$(CDC$_3$) 16.10 (2C, —OCH$_2$CH$_3$), 16.24 (2C, —OH$_2$CH$_3$), 24.81 (1C, m, —CH$_2$CHP$_2$) 34.11 (1C, t, JC-P =132.1, P—C—P), 49.93 (1C, t, $J_{C-P}$=7.8, —C(O)CHRC(O)), 62.66 (4C, m, —OCH$_2$CH$_3$), 67.11 (2C, —OCH$_2$Ph), 128.03 (4C, ortho C), 128.22 (2C, para C), 128.40 (4C, meta C), 135.12 (2C, 1' on Ph) and 168.41 (2C, —OC(O)CH); $\delta_P$(CDCl$_3$) 32.19; m/z (+ve ion FAB) (M$^+$+H) 585 (36), 369 (7), and 91 (100); HRMS (M$^+$+H) (Found: 585.20184 $C_{27}H_{39}P_2O_{10}$ requires: 585.20185).

EXAMPLE 7

Synthesis of Tetraethyl 3,3bis(phosphono)-propylidene bis(carboxylic acid) (22)

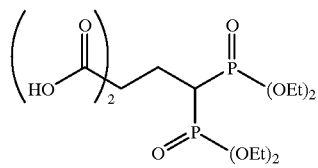

(22)

21 (0.698 g, 1.19 mmol), was dissolved in tetrahydrofuran (10 ml), and palladium activated charcoal (0.10g, cat.) added. The reaction mixture was stirred under an atmosphere of hydrogen, overnight, at room temperature. The reaction mixture was filtered and washed with saturated aqueous ammonium chloride (50 ml). The product was extracted into $CH_2Cl_2$ and dried with anh. $MgSO_4$, the solvent was removed under reduced pressure, and the product dried under high vacuum as a white solid, (0.42 g, 88% yield); $\delta_H$(MeOD) 1.35 (12H, t, J=6.6, —P—O—CH$_2$CH$_3$), 1.74 (2H, heptet, J=7.7, P$_2$CHCH$_2$CH—), 2.08 (1H, tt, $J_{P-H}$=23.1, J=6.6, P—CHRP), 3.18 (1H, t, J=6.6, —CH$_2$CH(CO$_2$H)2), 3.48–3.63 (8H, m, P—O—CH$_2$CH$_3$); $\delta$C(MeOD) 16.55 (2C, P—O—CH$_2$CH$_3$), 16.68 (2C, P—O—CH$_2$CH$_2$CH$_3$), 25.95 (1C, t, $J_{P-C}$=4.0, P$_2$CH CH$_2$CH—), 35.01 (1C, t, $J_{P-C}$=133.4, P—CHRP), 51.10 (1C, m, —CH(CO$_2$H)$_2$), 64.45 (4C, dd, J=9.4, 6.7, P—O—CH$_2$CH$_3$), 171.84 (2C, —CO$_2$H); $\delta_P$(MeOD) 22.8; m/z (+ve icon FAB) (M$^+$+D) 406 (100), and (M$^+$+H) 405 (90)

EXAMPLE 8

Synthesis of Tetrathyl 4,4-bis(phosphono)-butanoic acid (23)

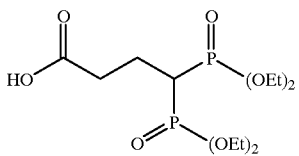

(23)

22 (0.200 g, 0.495 mmol), was heated to 130° C. for 3 hours, under a steady stream of nitrogen. The product was obtained as a colourless oil (0.174 g, 99%); $\delta_H$H(MeOD) 1.35 (12H, t, J=7.7, —OCH$_2$CH$_3$), 2.06–2.25 (2H, m, P$_2$CHC H$_2$CH$_2$—), 2.6–2.69 (1H, m, —CDHCO$_2$H), 2.81 (1H, tt, $J_{P-H}$=24.2, J=6.6, —PCHP—), 4.11–4.25 (8H, m, P—O—C H$_2$CH$_3$); $\delta_C$(MeOD) 16.57 (2C, P—O—CH$_2$CH$_3$), 16.71 (2C, P—O—CH$_2$CH$_3$), 21.82–2.10 (1C, m, P$_2$CH CH$_2$CH$_2$—), 32.53–33.07 (1C, m P$_2$CHCH$_2$CH$_2$CO$_2$H) 35.87 (1C, t, J=133.4, P—CHR—P), 64.07–64.36 (4C, m, —P—O—CH$_2$CH$_3$), and 175.85 (1C, —CO$_2$H); $\delta_P$(MeOD) 24.9m/z (+ve ion FAB) 361 (100) (M$^-$–H, for di-deuterated product); HRMS (+ve ion FAB) (Found: 363.12997 $C_{12}H_{25}D_2O_8P_2$ requires: 363.13067).

EXAMPLE 9

Synthesis of Tetraethyl {3-[3-benzoyloxy)estra-1,3,5-trien-17β-yloxycarb-c-yl]propylidene}bis [phosphonate](24)

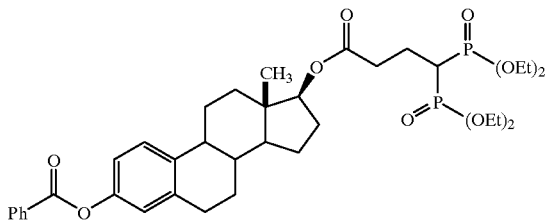

(24)

23 (0.071 g, 0.20 mmol, 1.0 equiv.), 3-O-benzoyl-17β-oestradiol (0.089 g, 0.24 mmol, 1.2 equiv.), and 4-(N,N-dimethylamino)pyridine (0.005 g, 0.04 mmol, 0.2 equiv.), were dissolved in $CH_2Cl_2$ (5 ml), and stirred at 0 ° C. under an atmosphere of nitrogen. EDCI (0.0455 g, 0.24 mmol, 1.2 equiv.), was added to the reaction mixture, and allowed to warm slowly to room temperature whilst stirring overnight. The reaction mixture was washed with water (30 ml), and the product extracted into $CH_2Cl_2$. The organic layer was collected, dried with anh. $MgSO_4$, and the solvent removed under reduced pressure. The crude product was absorbed onto silica gel and purified by silica gel flash column chromatography, 1–3% methanol/$CH_2Cl_2$ were used as eluents. The product dried under high vacuum and was isolated as colourless oil (0.048 g, 33%); $v_{max}$ 3053, 2983, 1729, 1601, 1243, and 1025; $\delta_H$(CDCl$_3$) 0.84 (3H, s, 18'—CH$_3$), 1.25–1.93 (11H, m), 1.35 (12H, t, J=7.2, P—OCH$_2$CH$_3$), 1.12–2.74 (7H, m), 2.87–2.92 (2H, m), 4.12–4.28 (8H, m, P—OCH$_2$CH$_3$), 4.70 (1H, dd, J=8.8, 7.1, 17'H), 6.92–7.00 (2H, m), 7.33 (1H, d, J=8.2, 1'H), 7.46–7.67 (3H, m), and 8.20 (2H, dt, J=8.3, 1.6, ortho H's on Ph); $\delta_C$(CDCl$_3$) 12.06 (1C, 18'—CH$_3$), 16.32 (2C, P—OCH$_2$CH$_3$), 16.43 (2C, P—OCH$_2$CH$_3$), 21.04 (1C, m, P$_2$CHCH$_2$CH$_2$—), 23.25 (1C), 26.03 (1C), 27.00 (1C), 27.59 (1C), 29.50 (1C), 35.68 (1C, t, J=132.1, P$_2$—CHR), 36.86 (1C), 38.18 (1C), 38.35 (1C), 42. 87 (1C), 43.98 (1C), 49.80 (1C), 62.61 (4C, t, J=6.7, P—OCH$_2$CH$_3$), 82.74 (1C, 17° C), 118.67 (1C), 121.58 (1C), 126.43 (1C), 128.49 (2C), 129.70 (1C), 130.10 (2C), 133.45 (1C), 137.84 (1C), 138.19 (1C), 148.68 (1C), and 172.72 (2C); $\delta_P$(CDCl$_3$) 23.2; m/z (+ve ion FAB) 721 (M$^+$+H, for product containing 2D), 720 (M$^+$+H, for product containing 1D), and 719 (M$^+$+H). The benzyl and ethyl groups can be removed by the methods of Examples 4 and 5.

EXAMPLE 10

Synthesis of Ethyl 17-oxoestra-1,3,5, -trien-3-yl proprionate (25)

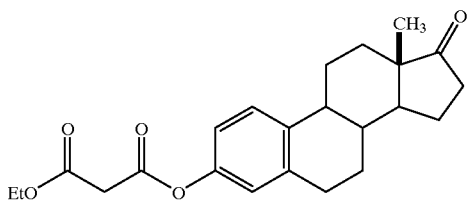

(25)

Oestrone (0.54 g, 2.0 mmol, 1.0 equiv.), triethylamine (0.56 ml, 0.405 g, 4.0 mmol, 2.0 equiv.), were dissolved in tetrahydrofuran (15 ml) and stirred at 0 ° C. under an atmosphere of nitrogen. Ethyl malonyl chloride (0.76 ml, 0.903 g, 6.0 mmol, 3.0 equiv.) was added slowly to the reaction mixture, which was allowed to warm to room temperature and stirred overnight. The reaction mixture was washed with water (2×50 ml), and the product extracted into CH$_2$Cl$_2$, and dried with anh. MgSO$_4$. The solvent was removed under reduced pressure, the crude product absorbed onto silica gel and purified by silica gel flash column chromatography, eluted with 0.5% methanol/CH$_2$Cl$_2$. The product was isolated as a colourless oil (0.144 g,19% yield); $\delta_H$(CDCl$_3$) 0.90 (3H, s, 18'—CH$_3$), 1.32 (3H, t, J=7.1, —OCH$_2$CH$_3$), 1.36–1.75 (6H, m), 1.88–2.59 (7H, m), 2.91 (2H, dd, J=8.3, 3.8), 3.59 (2H, s, malonate H), 4.26 (2H, q, 7.1, —OCH$_2$CH$_3$), 6.86–6.91 (2H, m), and 7.29 (1H, d, J=8.2, 1'H); $\delta_C$(CDCl$_3$) 13.65, 13.95, 21.41, 25.60, 26.13, 29.21, 31.39, 35.68, 37.83, 41.47, 43.98, 47.75, 50.26, 61.58, 118.35, 121.18, 126.30, 137.65, 138.00, 148.22 (3'C), 165.25 (—CO$_2$Et), 166.09 (—CO$_2$Ph), and 214.04 (17'C); m/z (+ve ion FAB) 385 (38) (M$^+$+H), 115 (100).

EXAMPLE 11

Synthesis of Tetraethyl [4-ethoxy-4-oxo-3-(17-oxoestra-1,3,5-trienyloxycarbonyl)-butylidene] bis [phosphonate] (26)

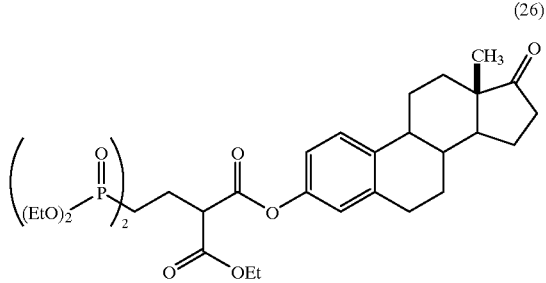

(26)

25 (0.112 g, 0.291 mmol, 1.0 equiv.), and 16 (0.087 g, 0.291 mmol, 1.0 equiv.), were dissolved in tetrahydrofuran and stirred at room temperature under an atmosphere of nitrogen. A solution of lithium bis(trimethylsilyl)amide (1M) in tetrahydrofuran (0.03 ml, 0.03 mmol, 0.1 equiv.) was added to the reaction mixture and stirred for 3 hours. The reaction mixture was quenched with saturated aqueous ammonium chloride, and the product extracted into CH$_2$Cl$_2$. The organic layer was collected and dried with anh. MgSO$_4$. The solvent was removed under reduced pressure and the crude product adsorbed onto silica gel. The product was purified by silica gel flash column chromatography, 0.5–3% methanol/CH$_2$Cl$_2$ as eluent. The product was isolated and dried under high vacuum to give a colourless oil (0.060 g, 30%); $\delta_H$(CDCl$_3$) 0.91 (3H, s, 18'—CH$_3$), 1.27–1.72 (8H, m), 1.37 (12H, t, J=7.2, P—O—CH$_2$CH$_3$), 1.90–2.95 (13H, m), 4.13–4.33 (11H, m), 6.82–6.90 (2H, m), and 7.30 (1H, d, J=8.8, 1'H); $\delta_C$(CDCl$_3$) 13.76 (1C, 18'C), 14.06 (1C, —CO$_2$CH$_2$CH$_3$), 16.24 (2C, —PO$_2$CH$_2$CH$_3$), 16.35 (2C, —PO$_2$CH$_2$CH$_3$), 21.53 (1C, P$_2$CHCH$_2$CH—), 24.96 (1C, m), 25.70 (1C), 26.24 (1C), 29.32 (1C), 31.50 (1C), 34.28 (1C, t, J=132.1, P—C—P), 35.76 (1C), 37.97 (1C), 44.11 (1C), 17.86 (1C), 49.93–50.23 (1C, m, —C(O)CHRC(O)—), 50.42 (1C), 61.77 (1C, —CO$_2$CH$_2$CH$_3$), 62.66–62.98 (4C, m, P—O—CH$_2$CH$_3$), 118.35 (1C), 121.18 (1C), 126.36 (1C), 137.70 (1C), 138.08 (1C), 148.38 (1C), 167.73 (1C),168.54 (1C), and 214.15; $\delta_P$(CDCl$_3$) 22.34, and 22.44; m/z (+ve ion FAB) 685 (57) (M$^+$+H), 239 (100); HRMS (Found: 685.29124 C$_{33}$H$_{50}$O$_{11}$P$_2$ requires: 685.29066).

(26) may be converted to the corresponding bisphosphonic acid by the method of Example 5.

EXAMPLE 12

Synthesis of Tetraethyl {3,3-bis[androst-4-en-3-one-17β-yloxycarbonyl]propylidene} bis[phosphonate] (27)

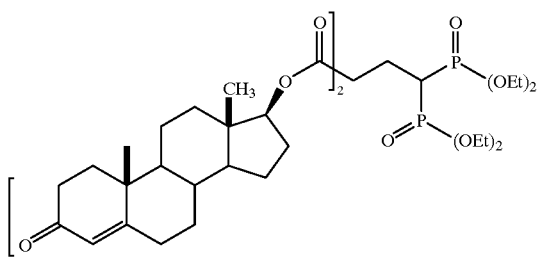

Testosterone (0.500 g, 1.73 mmol, 2.2 equiv.), 17 (0.363 g, 0.788 mmol, 1.0 equiv.), and 4-(N,N-dimethylamino) pyridine, were dissolved in toluene (7 ml) and heated under reflux, under an atmosphere of nitrogen. After 10 days reflux, more testosterone (0.250 g, 0.86 mmol, 1.1 equiv.) was added to the reaction mixture, and heated under reflux conditions for another 6 days. The reaction was stopped and washed with saturated aqueous ammonium chloride. The product was extracted into $CH_2Cl_2$ and dried with anh. $MgSO_4$. The solvent was removed under reduced pressure, and the crude product absorbed onto silica gel. The product was purified by silica gel flash column chromatography, 3% methanol/$CH_2Cl_2$ was used as the eluent. The product was isolated as a foam under a high vacuum (0.61 g, 82% based on 3); $\delta_H$(CDCl$_3$), 0.76 (3H, s, 18'—CH$_3$), 0.78 (3H, s, 18'—CH$_3$), 0.80–1.80 (20H, m), 1.12 (6H, s, 19'—CH$_3$), 1.28 (12H, t, J=7.2), 1.94 –1.98 (2H, m), 2.05 –2.57 (13H, m), 3.94 (1H, t, J=7.6, malonate H), 4.58 (2H, q, J=8, 17'H), and 5.66 (2H, s, 4'H); $\delta_C$(CDCl$_3$), 11.91 (1C), 12.02 (1C), 16.31 (2C), 16.42 (2C), 17.39 (2C), 20.49 (2C), 23.45 (2C), 24.82–25.02 (1C, m), 27.31 (2C), 31.43 (2C), 32.67 (2C), 33.88 (2C), 34.34 (1C, t, J=133.4), 35.34 (2C), 35.69 (2C), 36.53 (2C), 38.57 (2C), 42.56–42.72 (2C, m), 50.17 (2C), 53.61 (2C), 61.51 (1C), 62.61–62.92 (4C, m), 83.50 (1C), 83.64 (1C), 123.97 (2C), 168.80 (1C), 168.88 (1C), 170.77 (2C), and 199.37 (2C); $\delta_P$(CDCl$_3$), 22.98; m/z (+ve ion FAB3) (M$^+$+H) 946 (14), 703 (87), and 461 (100).

(27) may be convert=-d to the corresponding bisphosphonic acid by the method Example 5.

What is claimed is:

1. Bisphosphonate derivatives of hydroxy steroids which are bone resorption inhibitors or bone formation stimulators, the derivatives having at least one group A in place of a hydroxy group on the steroid molecule, where A is a group of the formula (A)

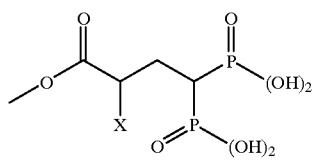

where X is:
(i) St—O—CO— where St is the residue of the hydroxy steroid given by removal of an OH group; or (ii) R$^1$—O—CO— where R$^1$ is an alkyl, alkenyl, cycloalkyl, aralkyl or aryl group, any of which may optionally be substituted;
and the salts and solvates of these compounds.

2. Compounds according to claim 1 wherein the steroid is an oestrogen, androgen, anabolic steroid, glucocorticoid or progestagen.

3. Compounds according to claim 1 wherein the steroid is 17 β-oestradiol, oestrone, testosterone, norethindrone, androsterone, norethandrolone or nandrolone.

4. A compound according to claim 1, said compound being:

(4)

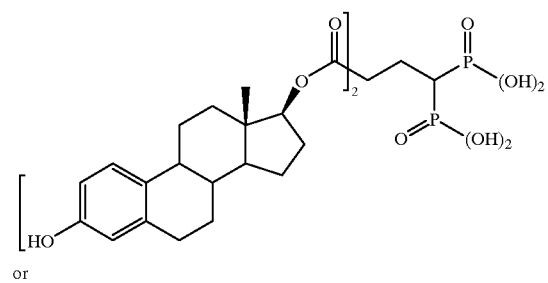

or (6)

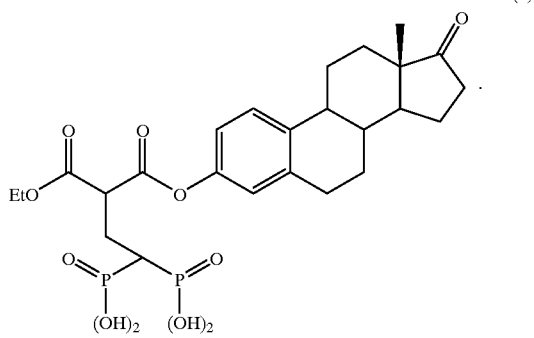

5. A pharmaceutical composition containing one or more compounds according to claim 1 and one or more pharmaceutically acceptable carriers, excipients or diluents.

6. Bisphosphonate derivatives of hydroxy steroids which are bone resorption inhibitors or bone formation stimulators, having a formula $$(St—O—CO)_2CHCH_2CH(PO(OH)_2)_2$$

where St is the residue of the hydroxy steroid given by removal of an OH group.

7. A pharmaceutical composition containing one or more compounds according to claim 6 and one or more pharmaceutically acceptable carriers, excipients or diluents.

8. A process for the preparation of a compound according to claim 1 which comprises:

(A) in the preparation of a compound in which X is a group (i), transesterifying the carboxylic ester groups of a compound of formula (7)

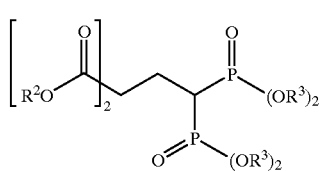

(7)

(where $R^2$ and $R^3$ are $C_{1-6}$ alkyl groups and may be the same or different) with the hydroxy steroid (StOH), to give a phosphonate ester (8) of the formula $(St-O-CO)_2CHCH_2CH(PO(OR_3)_2)_2$, followed by removal of the phosphonate ester groups by hydrolysis; or in the preparation of a compound in which X is a group (ii), reacting a malonate (13) of the hydroxy steroid $R^1$ CO.CH$_2$.CO.OSt     (13)

(where $R^1$ is as defined in claim 1) with a methylidene compound (10)

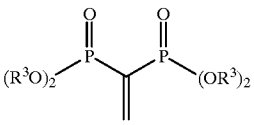

to give the addition product (14)

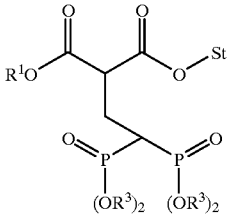

(14)

followed by removal of the phosphonate ester groups by hydrolysis.

* * * * *